United States Patent [19]

Bouriotis et al.

[11] Patent Number: 5,219,749
[45] Date of Patent: Jun. 15, 1993

[54] PROCESS FOR ISOLATING AND PREPARING PURIFIED CHITIN DEACETYLASE

[75] Inventors: Vassilis Bouriotis; Dimitri Kafetzopoulos, both of Crete, Greece; John Vournakis, Lyme, N.H.

[73] Assignee: Institute for Molecular Biology & Biotechnology/FORTH, Crete, Greece

[21] Appl. No.: 773,724

[22] Filed: Oct. 9, 1991

[51] Int. Cl.$^5$ .................. C12N 9/78; C12R 1/785; C12P 19/26
[52] U.S. Cl. ................... 435/227; 435/71.1; 435/84; 435/178; 435/259; 435/931; 536/20
[58] Field of Search ............. 435/227, 71.1, 84, 931, 435/259; 536/20

[56] References Cited

U.S. PATENT DOCUMENTS 4,282,351  8/1981  Muzzarelli ............... 536/20
4,368,322  1/1983  Muzzarelli ............... 536/20
4,958,011  9/1990  Bade ....................... 536/20

OTHER PUBLICATIONS

Pfaltz & Bauer Catalogue 1991/1992. 12th Ed. Div Aceto Chem Waterbury, Conn. 06708 p. 81 NBR C07640 "Chitin Deacetylated".
Master's Thesis of Stephen J. Lombardi.
Araki and Ito, *Methods in Enzymol.*, 161: 510-514 (1988).
Kauss and Bauch, *Methods in Enzymol.*, 161: 518-523 (1988).

*Primary Examiner*—Herbert J. Lilling
*Attorney, Agent, or Firm*—Hamilton, Brook, Smith, & Reynolds

[57] ABSTRACT

Chitin deacetylase, the enzyme that catalyzes the hydrolysis of acetamide groups of N-acetylglucosamine in chitin, was purified to homogeneity from mycelial extracts of the fungus *Mucor rouxii*. In addition, immunoglobulin specifically reactive with chitin deacetylase has been produced and purified.

4 Claims, 5 Drawing Sheets

PROCESS FOR ISOLATING AND PREPARING PURIFIED CHITIN DEACETYLASE

BACKGROUND OF THE INVENTION

Next to cellulose, chitin is the world's most abundant, easily obtained, and renewable biological material. It is a natural product synthesized by a wide variety of organisms. Several billion tons of the material are produced annually.

Chitin is a carbohydrate polymer, the N-acetylated polymer of β(1-4) linked N-acetylglucosamine, or poly-N-acetyl glucosamine. In plants, chitin is a cell wall constituent replacing cellulose or sometimes occurring together with cellulose. In animals, chitin is usually organized as a cuticle at one surface of the epithelial tissue. Although structurally similar to cellulose, chitin has distinctly different chemical properties. It is an extremely insoluble material, with limited industrial applicability.

The deacetylated derivative of chitin, chitosan, is a much more tractable material with a broad and impressive array of practical applications. Chitosan is positively charged, thus, it can be used as a protein precipitant and a metal chelating agent. It can be formulated as a solution, gel, membrane, film or fiber. Such formulations are useful, for example, in the areas of precious metal recovery, crop protection, chromatography and enzyme immobilization. Chitosan is a biologically benign, non-immunogenic, material making it ideal for use in the agricultural, food, drug and cosmetic industries. It can form complexes with other natural polymers, such as collagen and keratin, to form materials with unique biomedical properties. For example, such materials can be used as wound healing accelerants, components of artificial skin and blood vessels, anticoagulants, and controlled drug release vehicles.

At present the bulk of the chitosan produced worldwide is prepared from crustacean shell material. Chitin comprises about 20-50% of the dry weight of crustacean cuticles, the balance being primarily calcium carbonate, calcium phosphate and other proteins. Chitin is first isolated by treating ground crustacean shells with dilute acid and alkali to remove proteins and minerals. The raw chitin is then deacetylated by exposure to concentrated alkali at high temperature to generate chitosan. Although the chitosan produced in this manner has many useful features, it is impossible to effectively control the production process, which leads to the production of a material having a broad range of molecular weight and a heterogenous extent of deacetylation. Such a product is not of great value, since many of the potentially important applications, particularly in the biomedical area, require uniform material with very specific physical and chemical properties.

SUMMARY OF THE INVENTION

The subject invention relates to an essentially pure preparation of chitin deacetylase and to methods for isolating same from a cellular extract. In addition, the invention relates to immunoglobulin specifically reactive with chitin deacetylase. In another aspect, the invention relates to the use of the purified enzyme in a method for converting chitin to chitosan, and to the product produced by the method.

The purified enzyme is useful, for example, in the conversion of chitin to chitosan. The enzymatic conversion of chitin to chitosan provides an attractive alternative to presently employed chemical methods which suffer from a variety of technical drawbacks, some of which have been discussed above.

DETAILED DESCRIPTION OF THE INVENTION

Figure 1:
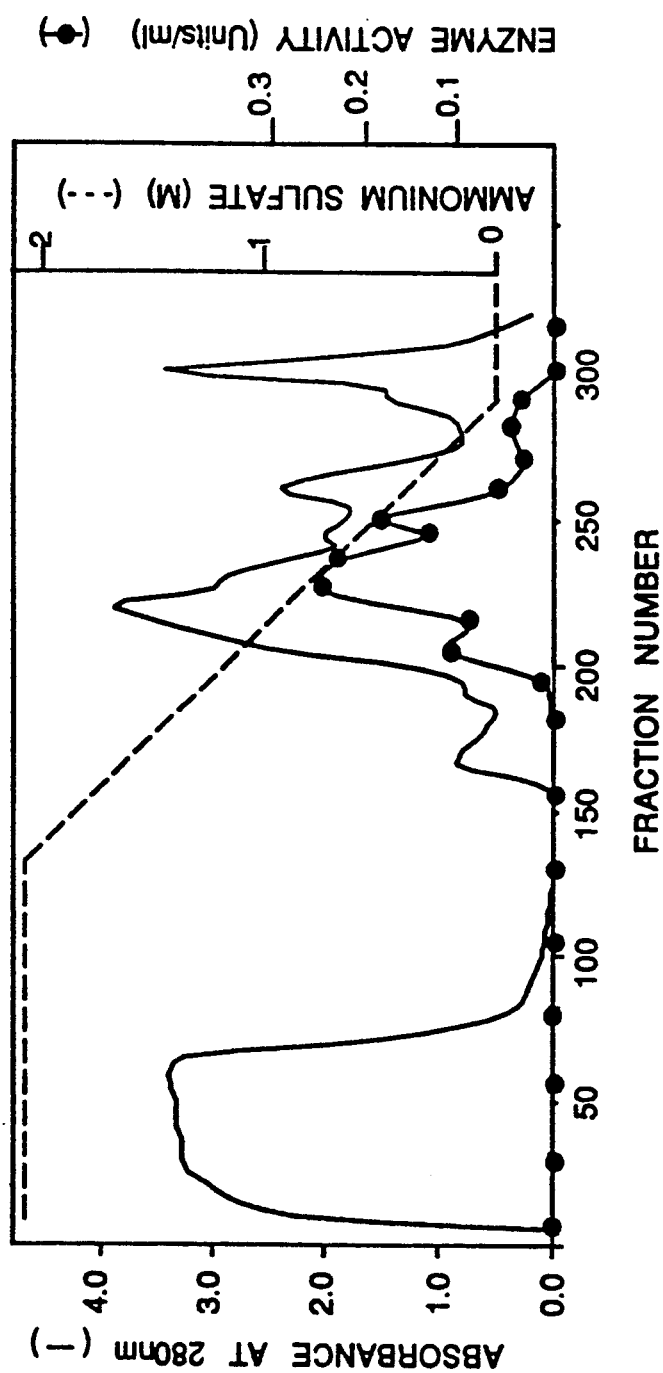
FIG. 1 is a diagram representing the elution profile from a Phenyl Sepharose ® CL-4B column.

The present invention was made possible by the discovery of a method for purifying chitin deacetylase from a cellular extract of an organism which produces chitin deacetylase. The enzyme chitin deacetylose is produced by a variety of genera including, for example, Mucor, Phycomyces, Absidia, and Choaneohora. Other potentially useful genera include Zygorhvnchus, Actinomucor, Circinella, Rhizoous, Colletotrichum and Rhizomucor.

A preferred source for chitin deacetylase is fungal mycelia. Such mycelia are produced in great quantities as a byproduct of the fermentation industry. The growth of *Mucor rouxii* in standard fermentors has been described in the literature. The use of a fungus such as *Mucor rouxii* offers a number of advantages. The organism can be grown using inexpensive nutrients. It can be grown to a high cell density (grams of cell dry weight per liter of culture medium) in a large scale fermentation system. The culture time required to achieve high cell density is as low as 12 hours/batch.

Initially, cellular extract is prepared from an organism which produces chitin deacetylase. For example, if the organism is a fungus (e.g., *Mucor rouxii*) mycelial cells are disrupted in the presence of an extraction buffer. The extraction buffer may contain protease inhibitors, other degradative enzyme inhibitors and stabilizers to maintain enzyme activity and facilitate its extraction. Non-soluble material is removed from the liquid phase of the extraction mixture, for example, by filtration or centrifugation.

The cellular extract is subjected to a thermal cycling step which results in the precipitation of undesirable protein (i.e., protein other than chitin deacetylase). For example, as described in the Examples below, the extract can be incubated at about 50° C. for a period of about 15-30 minutes. The precipitated protein is subsequently removed, for example, by filtration or centrifugation.

It is well known that the solubility properties of proteins in solutions having high salt concentrations vary over a wide range. This difference in solubility can be exploited to achieve separation of protein in a solution by precipitation at high ionic strength. Many salts can be used for this purpose, but ammonium sulfate is preferred by virtue of the fact that it does not appreciably alter pH, it is highly soluble, and it does not destabilize proteins.

Applicants' have determined that an ammonium sulfate concentration of about 2.1M effectively precipitated a wide variety of proteins from the liquid phase described above, without precipitating the chitin deacetylase. Proteins which precipitate in an ammonium sulfate concentration of about 2.1M are removed from the solution by standard techniques (e.g., filtration or centrifugation).

The liquid phase which is recovered following the ammonium sulfate precipitation is subjected to hydrophobic interaction chromatography. Hydrophobic interaction chromatography is widely employed for the purification of macromolecules on the basis of their varying strength of hydrophobic interaction with hydrophobic groups attached to an uncharged gel matrix. This technique is usually performed in the presence of moderately high concentrations of anti-chaotropic salts (salt promoted adsorption chromatography). Several factors influence the chromatographic behavior of proteins and peptides on hydrophobic adsorbents. These factors include ligand structure, ligand density, sample characteristics, flow rate, salting-out effect, ionic strength, temperature and pH. An example of a hydrophobic column resin is Phenyl Sepharose ® 6 Fast Flow. Material bound by a hydrophobic adsorbent is removed from the column by passing, for example, water over the column.

Following hydrophobic interaction chromatography, the solution containing the chitin deacetylase is further purified by ion-exchange chromatography. An ion exchanger is a solid support that has chemically bound charged groups to which ions are electrostatically bound. A negatively charged group will exchange positive ions and is a cation exchanger. A positively charged group will exchange negative ions and is an anion exchanger.

Ion exchangers can be characterized as strong or weak ion exchangers. Strong ion exchangers function over a wide pH range and thus are useful for isolating a weakly ionized substance that requires very low or high pH for ionization.

The pH of the material which is recovered from the hydrophobic column is adjusted to about 8 and passed over a strong anion exchange column (e.g., Q Sepharose ® Fast Flow). Fractions are collected and assayed for chitin deacetylase activity as described in the Exemplification section below. Fractions possessing chitin deacetylase activity are pooled and the pH of the pooled fractions is adjusted to about 3.5.

The solution is then passed over a column which contains a strong cation exchange resin (e.g., S Sepharose ® Fast Flow) and the flow through is collected. When analyzed by polyacrylamide gel electrophoresis, the flow through fraction contains an electrophoretically homogenous protein species. The term essentially pure, as used herein, refers to a chitin deacetylase preparation which resolves substantially as a single band when analyzed by gel electrophoresis.

In a second method of purification, Applicants have employed purified immunoglobulin specifically reactive with chitin deacetylase. Immunoglobulin having the desired properties can be produced by immunizing an animal with essentially pure chitin deacetylase. Immunoglobulin having the desired properties can be attached to a solid support to form an immunoadsorbent. The immunoadsorbent can then be used to purify the enzyme from a crude extract by conventional methods.

Chitin deacetylase, prepared as described herein, can be used in a method for converting chitin to chitosan. Reaction parameters affecting enzyme activity are discussed in the Examples.

EXAMPLES

Example 1

First Method for Purifying Chitin Deacetylase

Fermentation of *Mucor rouxii*

*Mucor rouxii* was obtained from the American Type Culture Collection (ATCC 24905). The fungus was grown in minimal medium as described by Bartnicki-Garcia and Nickerson (Bacteriol. 84: 841–858 (1962)) in 16 liters batches. Media was inoculated with $2 \times 10^8$ spores per liter and was stirred and aerated with sterile air for 24 hours at 28° C. Mycelia were harvested at mid-log phase by filtration. Cultures yielded approximately 20 gr of mycelia (wet weight) per liter.

Extraction and Purification of Chitin Deacetylase 400 g of mycelia were extracted by blending with 600 g of glass beads and 700 ml of extraction buffer containing 50 mM Tris HCl (pH 7.8), 100 mM NaCl and 0.2 mM PMSF for one hour over ice. After the extraction was completed the glass beads were settled and removed and the extract was centrifuged for 30 minutes at 8000 g at 4° C. The supernatant (750 ml) is referred to as the crude extract.

The crude extract was then incubated in a waterbath set at 50° C. for 30 minutes and the precipitated material was removed by centrifugation at 8000 g for 30 minutes at 4° C. The supernatant from the 50° incubation was made 2.1M in ammonium sulfate and the precipitated proteins were removed by centrifugation at 10000 g for 45 minutes. The supernatant (850 ml) was then passed over a column (44 × 230 mm) of Phenyl Sepharose ® CL-4B equilibrated with 20 mM Tris HCl (pH 7.5) containing 2.1M ammonium sulfate. After the column was washed with the buffer mentioned above, the retained proteins were eluted with a 2100 ml linear gradient of decreasing ammonium sulfate concentration. Flow rate was 250 ml/h and fractions of 14 ml were collected. The elution profile is shown in FIG. 1. Chitin deacetylase activity was detected in fractions 195–295 which were pooled for further purification. The protein content was followed by a UV monitor at 280 nm.

Chitin deacetylase activity was estimated using as substrate partially O-hydroxyethylated chitin (glycol chitin) radiolabeled in N-acetyl groups. The substrate preparation as well as the assay conditions were as described by Araki and Ito (*Eur. J. Biochem.* 55:71–78 (1975)) with the following modifications. The assay mixture contained 0.1 mg/ml BSA buffered by 25 mM sodium glutamate at pH 4.5 (50° C). Incubation time was 30 minutes at 50° C.

Figure 2:
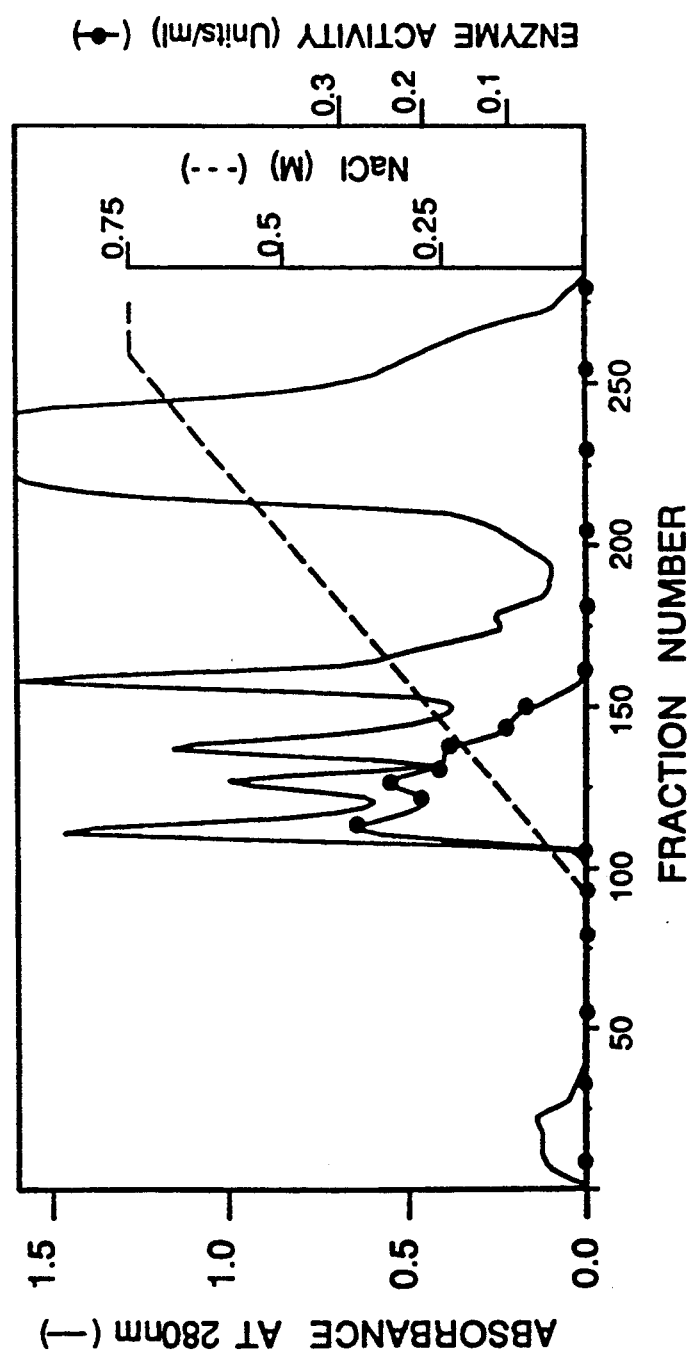
FIG. 2 is a diagram representing the elution profile from a Q Sepharose ® Fast Flow column.

The sample of partially purified chitin deacetylase from the previous step was dialyzed against 20 mM Tris HCl (pH 8), and then passed over a column of Q Sepharose ® Fast Flow (26 × 340 mm) equilibrated with the same buffer. After the column was washed, a linear gradient of NaCl (2000 ml, 0–0.75M) buffered with 20 mM Tris HCl (pH 8), was established. Flow rate was 300 ml/h and fractions of 11.5 ml were collected. The elution profile is shown in FIG. 2. Chitin deacetylase activity was detected in fractions 105–150 corresponding to −0.13M NaCl. These fractions were pooled for further processing.

Figure 3:
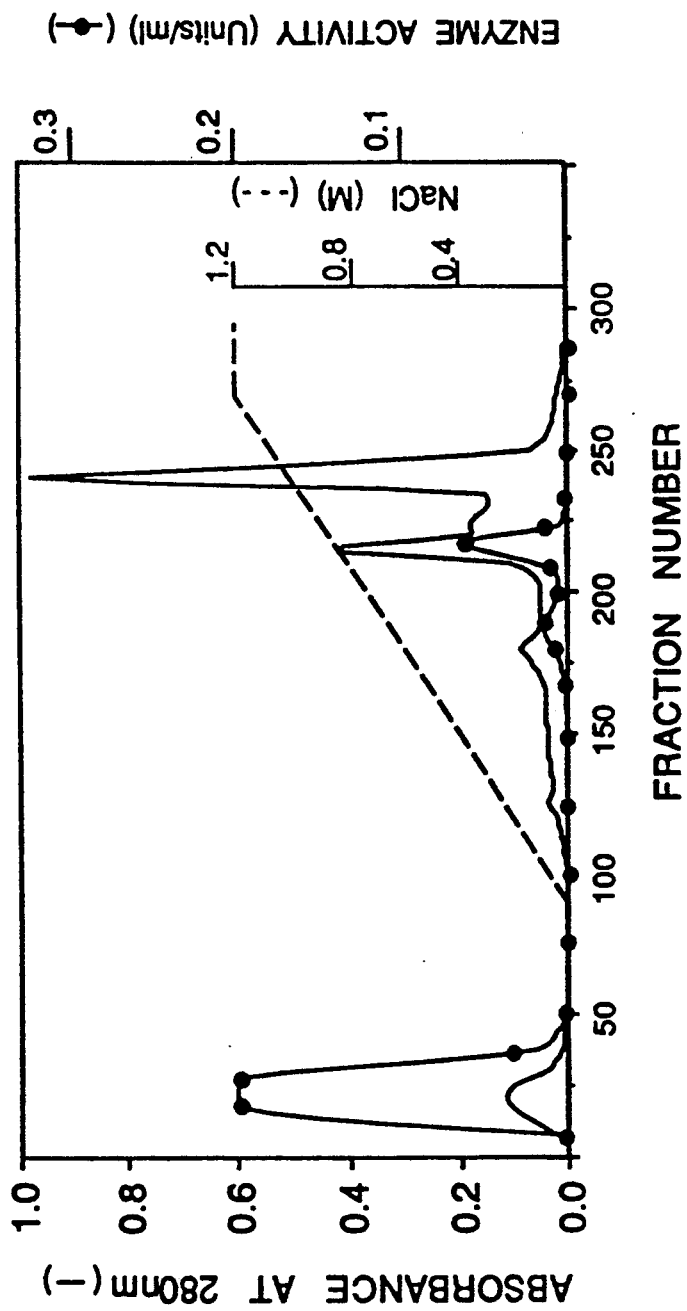
FIG. 3 is a diagram representing the elution profile from an S Sepharose ® Fast Flow column.
Figure 4:
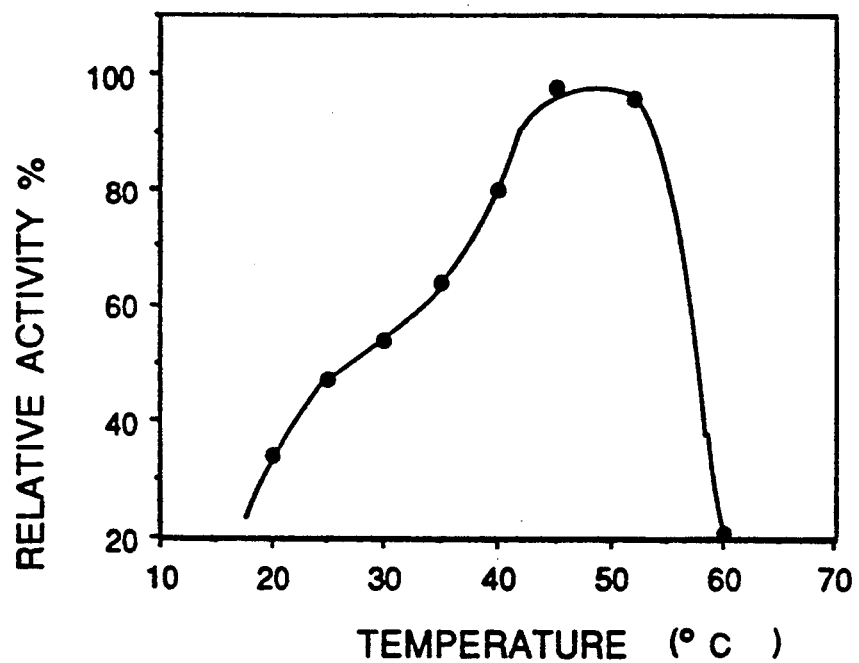
FIG. 4 is a diagram which represents the temperature dependence of chitin deacetylase activity.
Figure 5:
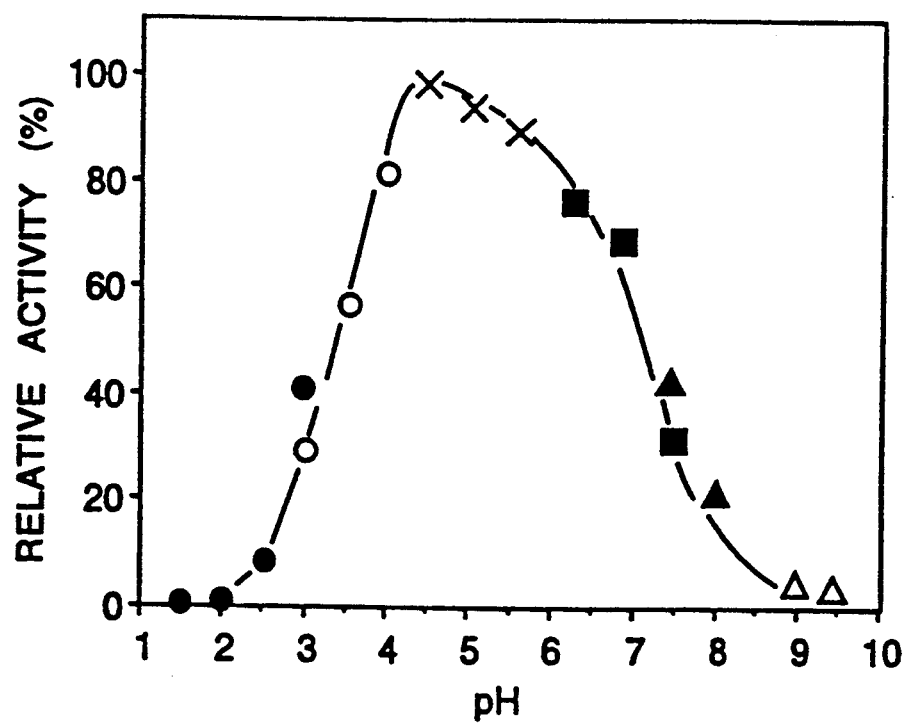
FIG. 5 is a diagram which represents the pH dependence of chitin deacetylase activity.

The pooled fractions were dialyzed against 25 mM sodium formate buffer, (pH 3.5), and the sample was loaded on an S Sepharose® Fast Flow column (26×280 mm) equilibrated with the same buffer. The column was eluted at a flow rate of 250 ml/h with a linear gradient of NaCl (2000 ml, 0–1.2M) in the buffer mentioned above. Fractions of 12 ml were collected. The elution profile is shown in FIG. 3. The majority of chitin deacetylase activity was not retained by the column and was detected in the flow through fractions in an electrophoretically homogenous form.

Characterization of Purified Enzyme a) molecular weight

The results of the purification scheme are summarized in Table 1. The enzyme purified by this procedure was judged to be electrophoretically homogeneous, as tested by both native and SDS-PAGE. On a gradient (5–20%) SDS polyacrylamide gel the enzyme band migrated at a distance corresponding to molecular weight of −75 kDa. When purified chitin deacetylase was subjected to gel filtration on Sephacryl® S-200 HR it was eluted as a single peak with an apparent size of −80 kDa indicating that the native enzyme exists as a monomer.

TABLE 1

Purification of chitin deacetylase

| Step | Total protein (mg) | Total enzyme activity (units[a]) | Specific activity units/mg | Yield % | Purification (-fold) |
|---|---|---|---|---|---|
| Crude extract | 10380 | 345 | 0.033 | 100 | 1 |
| 50° C. treatment | 4719 | 240 | 0.051 | 69.6 | 1.54 |
| Phenyl Sepharose® | 1374 | 150 | 0.11 | 43.5 | 3.3 |
| Q Sepharose® | 279 | 80 | 0.29 | 23.2 | 8.8 |
| S Sepharose® | 12.6 | 40.7 | 3.23 | 11.8 | 97.9 |

[a]One unit of the enzyme activity was defined as the amount of the enzyme required to produce 1 μmole of acetic acid per minute when incubated with 48 μg of glycol chitin under optimum pH (4.5) and temperature (50° C.) conditions.

b) carbohydrate content

Several pieces of evidence suggest that chiten deacetylase is a glycoprotein. After electrophoresis, the enzyme band gave a positive stain with periodate-Schiff's reagent on polyacrylamide gels. The enzyme was retained by a column of concanavalin A-Sepharose® 4B and recovered as a single peak by elution with a gradient of α-methyl mannoside at a position corresponding to approximately 25 mM. As shown in Table 2, direct carbohydrate analysis of the enzyme revealed that the protein contains 6 residues of fucose, 85 residues of mannose and 22 residues of N-acetylglucosamine per molecule contributing approximately 30% to its molecular weight. Sialic acid and other sugars were not found in significant amounts.

Monosaccharide analysis was carried out by gas-liquid chromatography and gas-liquid chromatography-mass spectrometry. The sample was hydrolyzed in 4M trifluoroacetic acid at 100° C. for 4 hours. The molar ratio of carbohydrates per molecule was estimated by direct carbohydrate and amino acid composition analysis.

TABLE 2

| Carbohydrate | mol/mol of protein | Nearest integer |
|---|---|---|
| Fucose | 5.81 | 6 |
| Mannose | 81.92 | 82 |
| N-Acetylglucosamine | 20.73 | 21 |
| Sialic acid | 0 | | c) immunoprecipitation of in vitro translation product

In order to determine the size of the chitin deacetylase polypeptide chain in an alternative manner, mRNA encoding the enzyme was translated in vitro followed by immunoprecipitation. mRNA was extracted from mycelia (15 g wet weight) harvested at the early log phase by grinding in liquid nitrogen. mRNA was purified by the guanidinium thiocyanate method of Chirwin et al. (Biochem. 18:5294–5299 (1979)) followed by pelleting in cesium chloride by ultracentrifugation. Poly (A) +RNA (−120 μg) was isolated by 3 passes through an oligo(dT)-cellulose column as described by Aviv and Leder (*Proc. Natl. Acad. Sci., USA* 69:1408–1412 (1972)). In vitro translation of total mRNA was performed using nuclease treated rabbit reticulocyte lysate according to the manufacturer's instructions. In vitro translation products were labeled with $^{35}$S-methionine.

Polyclonal antisera was prepared by emulsifying pure chitin deacetylase (500 μg, 1 mg/ml in PBS) with an equal volume of Freund's complete adjuvant. The mixture was injected intradermally into a rabbit after preimmune serum was obtained. The animal was reimmunized and bled after four and six weeks with 200 μg of enzyme in Freund's incomplete adjuvant, also injected intradermally. Antisera obtained were monitored for the presence of anti-chitin deacetylase antibodies by ELISA and by enzyme activity inhibition assays.

After the in vitro translation reaction was completed, 10μl of preimmune serum were added and the reaction was incubated for 30 minutes at room temperature. Antigenantibody complexes were removed by centrifugation after adsorption to 10 μl of Protein A-Sepharose® added to the reaction. Specific polyclonal antiserum (10 μl) was then added to the supernatant which was subsequently incubated as described above. The new antigen-antibody complexes were collected using protein A-Sepharose® by centrifugation and then washed three times with 20 volumes of 25 mM Tris HCl (pH 7.5), 150 mM NaCl by resuspension and pelleting. Immunoprecipitates were boiled for 5 min in SDS-PAGE loading buffer and analyzed by gel electrophoresis. The gel was fixed for 30 min in 10% acetic acid, 30% methanol, incubated for 30 min in EN$^3$HANCE® (New England Nuclear) and then dried and exposed.

In vitro translation products were analyzed on a 12% SDS polyacrylamide gel followed by autoradiography. The material immunoprecipitated by the specific antiserum showed one band corresponding to molecular weight of ∼49000 kDa that represents the size of the polypeptide chain prior to any post-translational modification.

d) enzyme activity characterization

The temperature optimum of the enzyme activity was estimated to be ∼50° C. using labeled glycol chitin, as substrate as described above. The temperature dependence of the chitin deacetylase activity is shown graphically in FIG. 1. The pH optimum was estimated to be ~4.5, tested with a combination of overlapping buffers, as shown graphically in FIG. 2. Chitin deacetylase (5 mU) when incubated with 1 mg of partially chemically deacetylated chitosan (81%) for one hour, released 0.22 moles of acetic acid corresponding to an increment of ~5.3% in deacetylation degree. The enzyme was also active on microcrystalline chitin (colloidal chitin) and carboxymethyl chitin (soluble derivative).

e) amino acid composition

The amino acid composition of chitin deacetylase is shown in Table 3. Basic amino acids accounted only for ~8% of the total amino acids, a value ~40% lower than the average.

Amino acid composition of purified chitin deacetylase was determined after 24 hour hydrolysis with 6M HCl at 100° C. The values are means of two different sample determinations. The number of residues per molecule of protein is based on the estimated molecular weight of 49000 Da from SDS-PAGE of the immunoprecipitated product from in vitro translation of mRNA.

TABLE 3

| Amino acid | Residues/molecule | Nearest integer |
| --- | --- | --- |
| Aspartic acid | 56.01 | 56 |
| Threonine | 55.65 | 56 |
| Serine | 59.23 | 59 |
| Glutamic acid | 37.33 | 37 |
| Proline | 29.08 | 29 |
| Glycine | 31.62 | 32 |
| Alanine | 56.73 | 57 |
| Valine | 27.58 | 28 |
| Methionine | 5.09 | 5 |
| Isoleucine | 20.40 | 20 |
| Leucine | 20.89 | 21 |
| Tyrosine | 16.24 | 16 |
| Phenylalanine | 8.78 | 9 |
| Histidine | 7.31 | 7 |
| Lysine | 15.85 | 16 |
| Arginine | 5.87 | 6 |
| Half-Cysteine | 9.62 | 10 |
| Tryptophan | 7.77 | 8 |
| Total | | 472 |

EXAMPLE 2

Production and Purification of Antibodies Reactive with Chitin Deacetylase

An adult male white New Zealand rabbit was immunized with 500 µg (1 mg/ml in PBS) of purified chitin deacetylase, prepared as described in Example 1, from the fungus *Mucor rouxii*. The enzyme was emulsified with an equal volume of Freund's complete adjuvant in a total volume of 1 ml, and was administered to the animal intradermally. A further three booster doses of 150 µg of chitin emulsified in Freund's incomplete adjuvant were administered at 4-week intervals. Test bleeds from the marginal ear vein were used to monitor serum antibody titer by ELISA. Control serum was taken prior to immunization.

The specificity of the antiserum produced was analyzed in a chitin deacetylase inhibition assay. Chitin deacetylase activity was assayed by measuring the radioactivity of [$^3$H]-acetic acid liberated from a watersoluble chitin derivative, glycol [acetyl-$^3$H] chitin. The reaction mixture contained 48 µg of glycol [acetyl-$^3$H] chitin, 1mM magnesium chloride, 0.1 mg/ml BSA and was buffered by 25 mM sodium glutamate (pH 4.5) in a total volume of 50 µl. After incubation at 50° C. for 15 min, the reaction was terminated by the addition of 16 µl of HCl, 4 µl of acetic acid and 80 µl of water. Ethyl acetate (0.5 ml) was added to the mixture, and the solution was vigorously mixed with a vortex mixer for 5 minutes and centrifuged at 14000 rpm. 4.5 ml of toluene-based liquid scintillation cocktail was added to 200 µl of the organic phase solution and swirled. The solution was transferred to a vial and measured for radioactivity in a liquid scintillation counter. One unit of enzyme releases 1.0 µmol of the acetic acid from glycol chitin per minute under the conditions described above. Specific activity was defined as the units of enzyme per milligram of protein. Protein was assayed by the so-called Lowry method using bovine serum albumin as a standard.

Antibody titer was monitored using a non-competitive ELISA. Chitin deactylase was immobilized onto microtiter plates (Maxi Sorp, Nunc, Denmark) at 2 µg/ml of "coating" buffer (pH 9.6), containing 0.05M sodium carbonate and sodium bicarbonate by incubation overnight at 4° C. Wells were washed out with 0.05% aqueous solution of Tween 80 followed by two washes with distilled water. After that 200 µl of blocking agent per well was incubated for 1 hour at room temperature. The blocking agent was 1 g of bovine serum albumin dissolved in 100 ml of 0.010M PBS (pH 7.4). Wells were washed out as before. An anti-rabbit IgG conjugated to horseradish peroxidase was used to indirectly detect specific IgG bound to immobilized chitin deacetylase. The conjugate was diluted 10,000-fold in 0.010 M PBS (pH 7.4) and incubated at 100 µl per well for one hour at room temperature. Wells were washed out with H$_2$O/Tween 80 solution as before, followed by two washes with distilled water. Wells were aspirated and incubated with 1001 of substrate/chromogen solution made up just prior to use as follows: The reaction was stopped after 15 minutes by addition of 50 µl of 4M sulfuric acid per well. Absorbance was read at 450 nm using an ELISA reader. The enzyme activity of a defined amount of purified chitin deacetylase was measured after incubation with various amounts of antiserum. These experiments confirmed that a component of the antiserum was specifically reactive with chitin deacetylase.

IgG was affinity-purified from rabbit serum using chitin deacetylase immobilized to cyanogen bromide-activated Sepharose 4B (Pharmacia Ltd.) according to manufacturer's instructions. A solution containing ten milligrams of purified chitin deacetylase was dialyzed against 2 lt of "coupling buffer" (pH 8.3), containing 0.1 M sodium bicarbonate and 0.5M sodium chloride. Preswollen cyanogen bromide-activated Sepharose 4B equilibrated with coupling buffer was mixed with chitin deacetylase (1.4 mg protein/ml of gel) overnight at 4° C. by end over end rotation. This mixture was transferred to a scintered glass funnel and sucked dry under vacuum. The fluid was recovered and assayed for protein to assess coupling efficiency. The gel was washed thoroughly with coupling buffer and mixed as before for 2 hours with Tris-HCl buffer (0.1 M, pH 8.0) at room temperature. The gel was sucked dry and washed with coupling buffer. Protein noncovalently adsorbed to the gel was removed by washing the gel with alternating buffers of low (0.1M sodium acetate, 0.5M sodium chloride, pH 4.0) and high pH (0.1M Tris, 0.5M sodium chloride, pH 8.3). The chitin deacetylase-linked Sepharose 4B was transferred to a mini-column and washed with 0.025M Tris-HCl (pH 7.4) which contained 0.02% sodium azide during storage at 4° C. The concentration of antibody in solution can be estimated by measuring $A_{280}$ using an average extinction coefficient for antibodies of 1.4 for 1 mg ml$^{-1}$ protein using a 1 cm path length cell.

Rabbit antiserum against chitin deacetylase obtained from various bleedings was separately precipitated by 40% saturation of ammonium sulfate. The immunoglobulin containing precipitate was dissolved and dialyzed extensively against 0.025M Tris (pH 7.4), 0.2M sodium chloride and subsequently passed through the chitin deacetylase-linked Sepharose 4B column (including protease inhibitors). The gel was washed with ten column volumes of 0.025M Tris, 0.1M sodium chloride (pH 7.4), until collected fractions gave negligible readings at 280 nm. Non-specifically bound proteins were eluted with 0.025M Tris, 1M sodium chloride, pH 7.4. A batch of IgG was eluted with two column volumes of 0.1M glycine-hydrochloric acid buffer (pH 2.8). A further batch of higher affinity IgG was eluted with two column volumes of 0.2M glycine-hydrochloric acid, pH 2.2. The term affinity, as used herein, refers to the functional affinity (avidity) as polyclonal antibodies were used. All fractions were immediately adjusted to pH 7.0 with 1M Tris - HCl (pH 9.0). The two populations of IgG fractions were pooled separately and concentrated by ultrafiltration prior to dialysis against 0.025M Tris (pH 7.4). The purified specific IgG shows the characteristic rabbit IgG pattern in SDS-PAGE. Pure specific IgG is stored at −20° C. at a concentration >1 mg/ml in 0.010M Tris, 0.1M sodium chloride (pH 7.4).

The coupling of chitin deacetylase to cyanogen bromideactivated Sepharose 4B was 90% efficient, producing chitin deacetylase-linked Sepharose 4 B at 1.4 mg of chitin deacetylase/ml of gel. By the method presented here, about 2.0–6.5 mg of pure specific IgG were isolated from every 10 ml of antiserum with the elution of pH 2.8 (2.0% to 5.0% of total protein after ammonium sulfate precipitation). Total isolated specific IgG represents 4.5% to 8.0% of total protein after ammonium sulfate precipitation. The binding capacity of the chitin deacetylase-linked Sepharose 4B for anti-chitin deacetylase antibody was determined at 1.4 mg IgG/ml of gel.

Example 3

Second Method for Purifying Chitin Deacetylase

Frozen mycelia (2 gr), prepared as described in Example 1, was thawed, minced and homogenized in 10 ml of 0.05M Tris-HCl buffer (pH 7.4) containing 0.5 mM PMSF, 0.01 mM NEM and 150 mM NaCl, using an improvised glass-bead miller (2 gr glass beads per gram of wet mycelia). All steps were performed at 4° C. This produced a homogenate which was centrifuged at 10,000 rpm for 30 minutes at 4° C. The supernatant (12.2 ml; 4.6 mg/ml; 56.0 mg) is referred to as the crude extract. The extract was then incubated in a waterbath set at 50° C. for 15 minutes and rapidly cooled in ice. Precipitated protein was removed by centrifugation at 35,000 rpm for 45 minutes at 4° C.

Five milligrams of the pure lower affinity rabbit IgG, described in Example 2, was dialyzed against the coupling buffer (pH 8.3) and mixed with 5 ml of swollen CNBr-activated Sepharose 4B to prepare an immunoadsorbent. The IgG was coupled by the method described for chitin deacetylase coupling. The coupling of IgG to activated Sepharose 4B was 85% efficient, producing IgG-linked Sepharose at 1 mg IgG/ml of gel. This immunoadsorbent was used for chitin deacetylase purification.

The supernatant described above (11.5 ml; 0.54 mg/ml; 6.2 mg) was loaded onto the immunoadsorbent (packed in a column of dimensions 2×1.6 cm; 5 ml) previously equilibrated in 25 mM Tris-HCl buffer (pH 7.4) containing 150 mM NaCl (buffer A). The column was washed with buffer A until no absorption of 280 nm was evident in the effluents (non-specifically bound proteins were eluted with 25 mM Tris-HCl pH 7.4, 1M NaCl). Specifically bound chitin deacetylase was eluted using 0.2M glycine-HCl buffer (pH 2.8) at a flow rate of 35 ml/h. Eluate was immediately adjusted to pH 7.0 with 1M Tris-HCl pH 9.0, dialyzed against buffer A and concentrated by ultrafiltration (300 μl; 40 μg/ml; 12 μg; 180 mU)

Purification of chitin deacetylase by immunoadsorption (table 4) produced a specific activity of 1500 m units/mg for the desorbed enzyme and a yield of about 30%. Assessment of chitin deacetylase purity by SDS-PAGE shows a single band. Purification of chitin deacetylase by conventional methods (table 1) produced a pure enzyme with a specific activity of 3.23 units/mg and a yield of 11.8%. The maximum binding capacity of the immunoadsorbent was determined at 42 μg of chitin deacetylase/ml of gel (4% of the antigen binding sites remain available for binding antigen after covalent immobilization to the matrix).

TABLE 4

| | Purification of Chitin Deacetylase By Immunoadsorption | | | | |
|---|---|---|---|---|---|
| Step | Total Protein (mg) | Enzyme activity (munits) | Specific activity (munits/mg) | Yield (%) | Purification (fold) |
| Crude extract | 56.0 | 608 | 10.86 | 100.0 | 1.0 |
| 50° C. treatment | 6.2 | 540 | 87.10 | 88.8 | 8.1 |
| Immunoadsorbent | 0.012 | 180 | 1500.00 | 29.6 | 1400.0 |

Equivalents

Those skilled in the art will know, or be able to ascertain, using no more than routine experimentation, many equivalents to the specific embodiments of the invention described herein. These and all other equivalents are intended to be encompassed by the following claims.

We claim:

1. A method for isolating essentially pure chitin deacetylase comprising:
   a) providing a cellular extract from an organism which produces chitin deacetylase;
   b) adding ammonium sulfate to the cellular extract to a concentration of about 2.1 M;
   c) removing non-soluble material from the liquid phase;
   d) passing the liquid phase from step c) over a hydrophobic column;
   e) eluting the bound material from the hydrophobic column;
   f) adjusting the pH of the eluted material from step e) to produce a solution having a pH of about 8;
   g) passing the solution from step f) over a strong anion exchange column;
   h) collecting fractions from the strong anion exchange column and pooling fractions with chitin deacetylase activity;

i) adjusting the pH of the pooled fractions from step h) to about 3.5;
j) passing the solution from step i) over a strong cation exchange column and collecting the flow through.

2. A method of claim 1 wherein the organism is *Mucor rouxii*.

3. A method for isolating essentially pure chitin deacetylase from a fungus which produces the enzyme comprising the steps of:
   a) providing mycelia from a fungal culture;
   b) disrupting the mycelia in an extraction buffer;
   c) removing non-soluble material from the liquid phase;
   d) incubating the liquid phase from step c) at a temperature of about 50 degrees C. for about 30 minutes;
   e) removing non-soluble material from the liquid phase;
   f) adding ammonium sulfate to the liquid phase from step e) to a concentration of about 2.1M;
   g) removing non-soluble material from the liquid phase;
   h) passing the liquid phase from step g) over a hydrophobic column;
   i) eluting the bound material from the hydrophobic column;
   j) adjusting the pH of the eluted material from step j) to produce a solution having a pH of about 8;
   k) passing the solution from step j) over a strong anion exchange column;
   l) collecting fractions from the strong anion exchange column and pooling fractions with chitin deacetylase activity;
   m) adjust the pH of the pooled fractions from step l) to about 3.5;
   n) passing the solution from step m) over a strong cation exchange column and collecting the flow through.

4. A method of claim 3 wherein the fungus is *Mucor rouxii*.

* * * * *